United States Patent [19]

Petty-Saphon et al.

[11] Patent Number: 5,737,774
[45] Date of Patent: Apr. 14, 1998

[54] DEVICE FOR PREVENTING OR REDUCING THE INCIDENCE OR INTENSITY OF PAIN IN THE BODY

[75] Inventors: Satham Petty-Saphon, Saffron Walden, England; Tommy Hansson, Gothenburg, Sweden

[73] Assignee: Spine-Issimus Limited, Saffron Walden, England

[21] Appl. No.: 897,966

[22] Filed: Jul. 21, 1997

Related U.S. Application Data

[63] Continuation of Ser. No. 307,458, Sep. 19, 1994, abandoned.

[30] Foreign Application Priority Data

Sep. 18, 1993 [GB] United Kingdom ............ 9319288
Jan. 21, 1994 [GB] United Kingdom ............ 9401176

[51] Int. Cl.$^6$ .............. A61F 7/00; A41D 13/00; A41D 27/00
[52] U.S. Cl. .............. 2/69; 2/455; 2/463; 2/44; 2/467; 602/2; 602/7; 602/8; 604/289; 604/291; 607/114
[58] Field of Search .............. 2/44, 92, 60, 91, 2/129, 207, 916, 920, 903, 904, 908, 455, 456, 457, 458, 459–467, 1, 69; 602/17, 19, 1, 2; 604/291, 289; 607/96, 114; 450/155

[56] References Cited

U.S. PATENT DOCUMENTS

| | | | |
|---|---|---|---|
| 3,696,810 | 10/1972 | Gaylord, Jr. | 602/18 |
| 3,717,143 | 2/1973 | Johnson | 602/19 |
| 4,006,741 | 2/1977 | Arluck | 128/90 |
| 4,232,663 | 11/1980 | Newton | 602/18 |
| 4,336,807 | 6/1982 | Benckhuijsen | |
| 4,460,645 | 7/1984 | Jones et al. | 428/323 |
| 4,470,417 | 9/1984 | Gruber | |
| 4,475,543 | 10/1984 | Brooks et al. | 602/19 |
| 4,572,167 | 2/1986 | Brunswick | 602/19 |
| 4,676,233 | 6/1987 | Scheunberg | 128/87 R |
| 4,894,865 | 1/1990 | Ieraci | |
| 5,072,455 | 12/1991 | St. Ours | 2/81 |

FOREIGN PATENT DOCUMENTS

| | | |
|---|---|---|
| 0 019 822 A1 | 12/1980 | European Pat. Off. . |
| 0 454 184 | 10/1991 | European Pat. Off. . |
| 2 617 707 | 1/1989 | France . |
| 2 648 343 | 12/1990 | France . |
| 507215 | 6/1939 | United Kingdom . |
| 873575 | 7/1961 | United Kingdom . |
| 1038043 | 8/1966 | United Kingdom . |
| 1347554 | 2/1974 | United Kingdom . |
| 2 027 585 | 2/1980 | United Kingdom . |
| 1605045 | 12/1981 | United Kingdom . |
| 2 193 429 | 2/1988 | United Kingdom . |
| 2193429 | 2/1988 | United Kingdom ............ 2/92 |
| 2 261 822 | 6/1993 | United Kingdom . |
| 88 00818 | 2/1988 | WIPO . |
| 93 12735 | 7/1993 | WIPO . |

*Primary Examiner*—Jeanette E. Chapman
*Attorney, Agent, or Firm*—Bacon & Thomas

[57] ABSTRACT

A device for preventing or reducing the incidence or intensity of pain occurring in a region of the body of a wearer, includes insulating material (2) which is arranged to be worn in conformity and close proximity with the body region. The insulating material has at least one layer (14) for reducing heat loss from the body region by convection and at least one reflective layer (13) for reducing heat loss from the body by radiation, whereby a targeted local warming effect is achieved in the body region such that the skin and underlying musculoskeletal structures are in such an active state that they can function properly to provide a clinical benefit to the body region.

18 Claims, 3 Drawing Sheets

DEVICE FOR PREVENTING OR REDUCING THE INCIDENCE OR INTENSITY OF PAIN IN THE BODY

This application is a Continuation of application Ser. No. 08/307,458, filed Sep. 19, 1994, now abandoned.

BACKGROUND OF THE INVENTION

1. Field of the Invention

This invention relates to a device for preventing or reducing the incidence or intensity of pain occurring in the body, for example in the neck, back (high-back or mid-back or low-back) or in the joints of a wearer.

2. Discussion of the Prior Art

In the past various devices and techniques have been used with the aim of treating body pain, for example in the back. Conventionally such devices are belts or collars which have mechanical support to resist movement of the neck or back. These devices may be made from a mechanically reinforced fabric which is distributed within the entire collar or belt. These collars and belts are generally also porous allowing aeration and heat passage.

Heat or cold has been thought to have a pain reducing effect. For example, in self-care, heat is a widely used method as can be seen with electric pads, hot water bottles, hot baths and saunas.

Several devices exist on the market for applying heat to the back. These include hot water bottles, hot pads powered by electricity or chemical reactions.

They have the disadvantages that (a) an external source of heat is required for application to the back for pain relief; (b) they do not have any specific thermal insulating capacity and the heat remains only for a limited period of time; and (c) they are heavy, bulky and cumbersome.

Instead of using an external source of heat it is also known to keep the whole body warm simply by wearing clothes, coats or blankets. Various fabrics have been used from wool to synthetic materials such as acrylics and hollow fibres. Conventionally they cover a large portion of the body and the thermal characteristics of the worn articles are generally ill-defined and a targeted, local warming effect is not achieved.

There have also been many efforts aimed at achieving a targeted local warming effect (GB-A-873,575, GB-A1,038, 043, FR-A-2,617,707). The materials used have low insulating characteristics or their insulating characteristics are ill-defined.

There have also been efforts to achieve both insulation and mechanical support. GB-A-1,347,554 and EP-A0,019, 822 are examples of such attempts. In those disclosures heat is applied externally (not provided by the body itself). In both of these documents, the source is electrostatic friction of the clothing materials between themselves and the body of the wearer.

However none of the above described arrangements is likely to be clinically effective as the materials suggested by the documents have an insufficient warming effect. Typical thermal conductivity values of the insulating materials are likely to be well in excess of 0.4 cm/TOG or 0.04 W/m° C. (TOG is the thermal resistance which is equal to 10 times the temperature difference between two faces of the test speciman when the peak flow is 1 Watt/m$^2$. TOG is expressed as 0.1 (m$^{2\circ}$ C.)/W. TOG values take no account of the thickness of the material but the thermal conductivity expressed as cm/TOG does. Thermal conducitivity is the conductivity for 1 cm material thickness). Furthermore, the density is likely to be around 40 Kg/m$^3$. Thus to get the requisite targeted local warming effect would require a large thickness. This would make any such device heavy and bulky and not convenient to use. The materials suggested in these documents tend to reduce heat loss only through convection (insulation through air).

SUMMARY OF THE INVENTION

It has been appreciated by the inventors that account should be taken of the fact that heat loss can also occur through means other than convection and conduction, notably through infra-red radiation. The inventors have also appreciated that the manner in which the insulating materials are used, e.g. taking into account the distance between the skin and insulating materials or the curved shape of the back itself, is of importance. Furthermore, it has also been realised that a constant and targeted warming effect on regions of the body may have preventative or therapeutic advantages.

In the absence of strenuous exercise the largest portion of heat loss from an animal or human being is through radiation. It has been found to be between 40% and 80% depending on the clothing and environmental conditions and the body condition itself. To increase the skin and underlying body temperatures or maintain them constant, one can of course consider wearing thick clothes. However clothes might not bring the temperature to the level desired as they are insulating by virtue of convection reduction. An alternative solution would be to wear reflective materials, ie. materials which reflect infrared body heat radiation. This reflection serves to 're-heat' the body once the reflected radiation returns to its source minimising therefore unnecessary additional heat generation by the body and maximising heat preservation. Although such materials are known, because they have been used in space research, as emergency blankets and for clothing articles, they have been used primarily as an overlay over the overall body. They have not been applied to the back or other parts of the body for a specific clinical purpose and indeed they are unlikely to have achieved any clinical benefit. In particular, the use as an overlay of such materials has several implications. There is always a space gap between the materials and the body and this space gap is variable depending on the movement of the body or on the environment (wind, draught etc). The area through which body radiation is emitted increases with a space gap and there is a greater likelihood that the radiation does not encounter the reflective layers or if it does, that the reflected radiation does not return back to the body. This effect is exacerbated when there are curvatures in the heat emitting parts such as the lumbar portion of the back or the posterior neck or in the reflective surfaces. In addition the layers of materials between the body and the reflective layers (interspace materials) absorb radiation. The re-emission of infra-red radiation is reduced accordingly and is also more scattered. This therefore leads to a decrease of net radiation received by the reflective layers and by the body. The absorption by the interspace materials contributes furthermore to heat losses through convection, either free (still air moving by virtue of its density changes with temperature) or by forced convection through air movements. The inventors have realised that the arrangement and position of reflective material with respect to the body is critical to its performance and this had not been taken into account by any of the known arrangements. Furthermore the inventors have realized that considerable benefit may be achieved in such circumstances if the skin temperature is increased to and preferably maintained at an optimal level.

According to a first aspect of the invention, there is provided a device for preventing or reducing the incidence or intensity of pain occurring in a region of the body of a wearer, said device comprising insulating material which is arranged to be worn in conformity and close proximity with the body region, said insulating material having means for reducing heat loss from the body region by convection and reflective means for reducing heat loss from the body by radiation, whereby a targeted local warming effect is achieved in said body region such that the skin and underlying musculoskeletal structures are in such an active state that they can function properly to provide a clinical benefit to the body region.

By placing the insulating material in close contact and conformity with the targeted body region, not only is radiation loss reduced (because of the reflective means) but also convective heat loss is also reduced. Curvatures of, and the relative distances between, the body and insulating parts are also relevant for convection loss reduction together with the inherent quality of the insulating material itself in entrapping air.

Porosity for water vapour permeability as well as water low retention for reducing losses due to conduction are also relevant. Indeed embodiments of the present invention will also reduce heat losses due to conduction. This property may be inherent in the insulating material providing the radiative and convective insulation. Alternatively the insulating material may also include further means for reducing heat losses due to conduction.

It is preferred that the temperature of the skin be at least above the 33° C. level, preferably 34° C. and above. At these temperatures the underlying musculoskeletal structures are likely to be kept active such that they can function properly to prevent injury or assist in improving posture to reduce the incidence of pain or in relaxing abnormal stresses to reduce the intensity of pain. It will be appreciated that in extreme conditions, it may be difficult to maintain the skin temperature at 33° C. Nevertheless such embodiments may still be of clinical benefit to the wearer.

Preferably the thermal conductivity of the insulating material in use should be less than 0.35 cm/TOG or 0.035 Watt/(m° C.). The distance between the body region and the device is preferably 10 mm or less. The layers between the body and the device are preferably as few as possible and as thin as possible (such as a thin undervest or nothing at all as the device is to be used preferably against the skin or over an undervest). The density of the insulating material is preferably less than 12 kg/cubic meter. The weight of the insulating material in the device is preferably between 15 and 30 grams, for example about 22 g, to make the device lightweight and convenient to use. The thickness of the insulating material is preferably no more than 2 cm. The overall thickness between skin and the outer surface of the device is preferably no more than 3 cm.

Additionally, the device may incorporate mechanical support elements designed to prevent excessive motion known to be detrimental for example to the back or neck. Alternatively or additionally such supports may be aimed at reminding the wearer of excessive detrimental motion. Thus, the device optionally has mechanical rigidity to resist flexion/extension or torsion.

Embodiments of the present invention may provide a lightweight and easy to use device to prevent or reduce the incidence or intensity of pain occurring in regions of the body for example in the neck, upper, middle or low back of a wearer. It is for example a belt to be worn around the back, a collar to be worn around the neck or a device to be worn around joints such as the knee, ankle and elbow. The device preferably is attachable firmly and conveniently to the body. The insulating materials within the device preferably comprise materials of low thermal conductivity based on the combination of reduction of heat losses through radiation, convection and conduction.

One embodiment of the device is of a belt design to be worn in the lower back region. It may have a larger posterior surface containing the insulating material which should cover the lumbar spine and upper sacrum and the peripheral muscles. The belt is preferably fastened through a Velcro® mechanism (hook and loop fastening system). Braces to be worn over the shoulders may additionally be provided.

The insulating material may be a multi-layer polypropylene fibre matrix such as Flectalon® or an organised reflective/convective insulation multi-layer arrangement. Such a reflective layer may be a perforated aluminised plastic or fabric film. The convective insulation layer may be a microfibre matrix like Thinsulate® (3M Company).

The fabric enclosing the insulating material may be any conventional fabric used in garments, but is preferably stretchable. The degree to which the fabric may stretch depends on the construction of the device. For example, if the device has two elasticated portions which are used to retain the device in place, then the fabric may only be slightly stretchy. If these two portions are not elasticated, then the fabric may be very much more stretchable and is, for example, a Lycra® power net.

Where the device is to be worn in the posterior neck portion of the body, the insulating material may be conveniently placed against the cervical and upper thoracic spine and the peripheral muscles.

In another embodiment of the invention, the insulating material is incorporated in a work garment which has a pocket designed to accept the insulating material and an external belt to bring the insulating material into proximity with the skin and make it conform to the body.

In a further embodiment of the invention the insulating material is incorporated in underwear such as pants and vests or tight garments as commonly used in athletics and cycling. These pants and vests are conveniently modified to bring the insulating material in proximity and conformity with the body part of interest such as the neck, the upper or lower thoracic spinal regions, without however making the wearer uncomfortable or feel hot in body parts of lesser interest.

The device may be additionally attached to the body through the use of braces over the shoulders.

BRIEF DESCRIPTION OF THE DRAWINGS

Certain preferred embodiments of the invention will now be described with reference to the accompanying drawings in which.

DETAILED DESCRIPTION OF THE PREFERRED EMBODIMENTS

Figure 1:
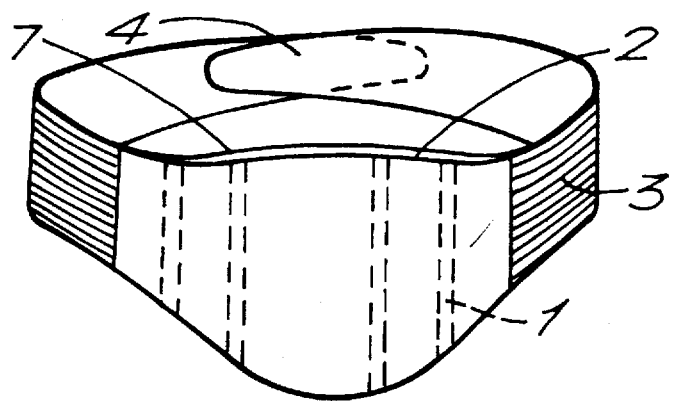
FIG. 1 shows a perspective view of a first embodiment of the invention in the form of a corset.

FIG. 1 shows a perspective view of one design of a device in the form of a belt or corset. The device incorporates a posterior mechanical support in the form of longitudinal steel strips 1 to reduce flexion or extension and/or simply to make the person wearing the corset feel uncomfortable with flexion or extension. Four strips are shown, arranged in two pairs, but in an alternative embodiment each pair may be replaced by a single strip, to provide a device with two strips. Other numbers of strips are also possible. The strips are incorporated within a fabric which is sufficiently close to the body to achieve the effects described above. Conveniently, the mechanical support strips 1 are placed on the anterior side of the device facing the skin (see FIG. 8 or 9). These are preferably made from flexible stainless steel of the type which is known in the trade as Flexisteel or Nulybone.

Away from the posterior body, and next to the strips 1 (including spacers 16 which can be seen from FIG. 8) and the surrounding fabric 7 is the insulating material 2 which may be a metallised, multi-layered plastic fibre matrix such as described in more detail hereinafter with reference to FIGS. 5 to 7. The multi-layer fibre-matrix entraps air and the metallised surface reflects back the body heat providing a very effective insulation which helps to keep the posterior spinal region constantly warm. The belt has a pocket (not shown) at the posterior portion which contains the insulating material of a shape and size sufficient to cover the relevant body parts.

The portion of the device not facing the posterior portion of the body is of a design which allows the device to be easily fitted and worn conveniently and comfortably. In particular, the portion of the device which holds the insulating material is attached at either end 3 to an elasticated fabric which allows the device or collar to be tightened. Through stretching and fastening actions the device is made to conform to the body. A stretchy fabric may of course cover the insulating material, in addition to the elasticated fastening portions. This elasticated material has Velcro® at each end 4 to facilitate fastening.

Figure 4:
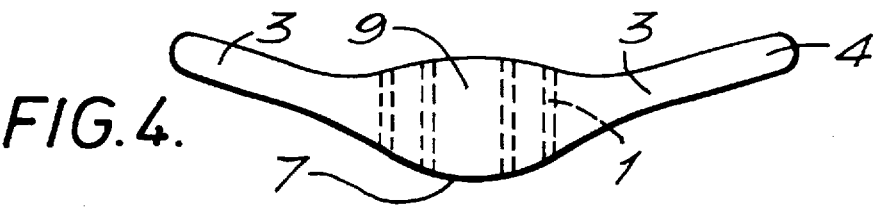
FIG. 4 shows a plan view of the first embodiment, when opened out and laid flat.
Figure 10:
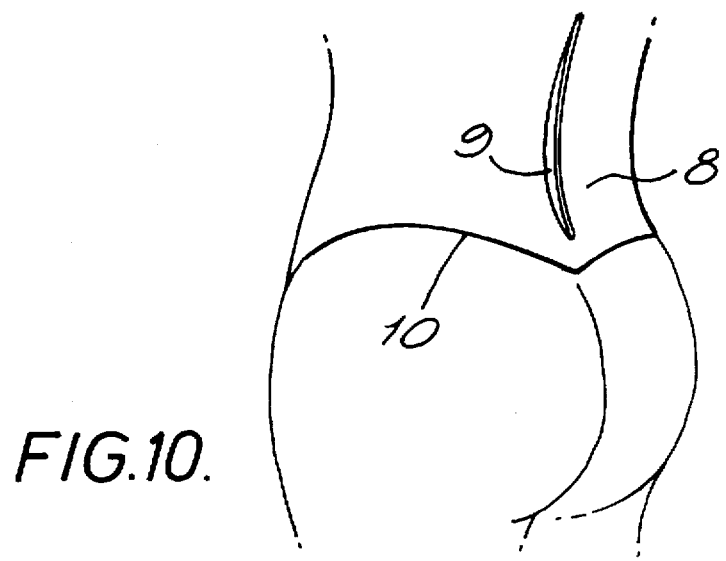
FIG. 10 shows a perspective view of a back.

As can be seen from FIG. 4, the device has, in plan view, a generally V-shape with narrower wings to conform to the shape of the back, as shown in FIG. 10, which allows the device to be easily worn by both men and women. These features enable the wearer to wear the belt comfortably without sweating laterally or anteriorly.

The device incorporating the insulating material is to be attached to the lumbar body such that the insulating material conforms to the body and is placed at a relatively short distance from the skin. Through the stretching action any fabric worn between the body and the device such as a vest will be flattened making it as thin as possible, preferably to less than 8 mm thickness, which is judged as optimum for convective and conductive insulation. Preferably the device is used directly against the skin or over an undervest. The overall thickness between the skin and the outer insulating material layer of the device is therefore less than 3 cm.

The longitudinal flexible steel strips 1 can be replaced by strips or bands placed diagonally from inferior left to superior right and vice versa to resist torsion or these can be added to the longitudinal strips to resist flexion/extension as well as torsion. Instead of being made from flexible steel these strips can also be made from strong elastic materials.

It is clear that other forms of the device following similar principles can also made to provide a collar for the neck or a device for other joints, to provide a targeted local warming effect and the desired clinical benefit.

It will be appreciated that the mechanical support materials can also be omitted from embodiments of the invention.

Figure 2:
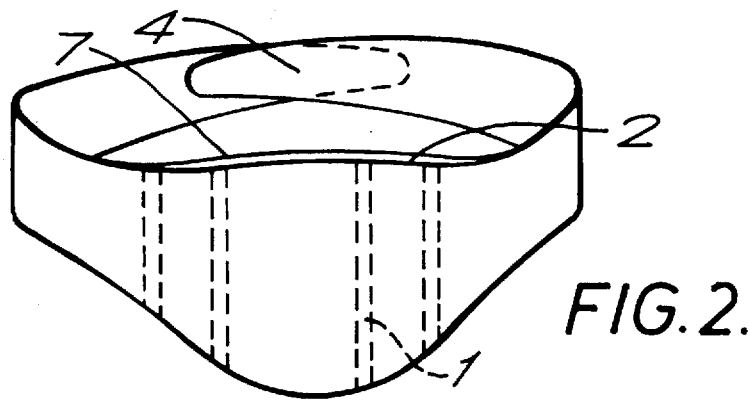
FIG. 2 shows a perspective view of a second embodiment of the invention, which is similar to the first.

FIG. 2 shows a device of a design similar to that of FIG. 1 except that it has no elasticated portions. Rather, the material facilitating stretching is the lining fabric itself and forms part of the corset or belt or collar. This fabric can be less elastic than the material used in the end portions of the first embodiment. The fabric may be a porous, breathable stretchable fabric such as Lycra® or a Lycra® power net which can be stretched to provide body proximity and conformity. One of the advantages is that the manufacture of this device is likely to be simpler with this type of design.

Figure 3A:
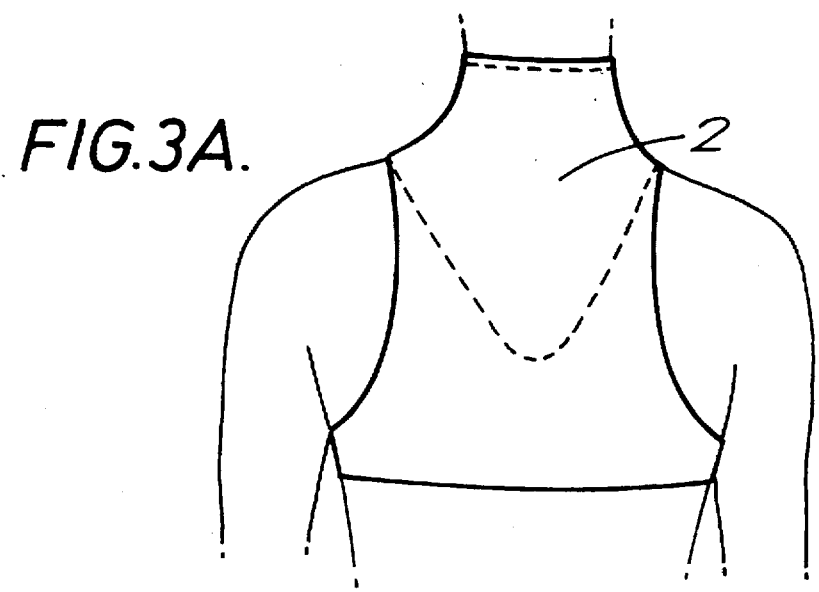
FIGS. 3A and 3B show rear elevation views of third and fourth embodiments of the invention, in the form of modified undervests.
Figure 3B:
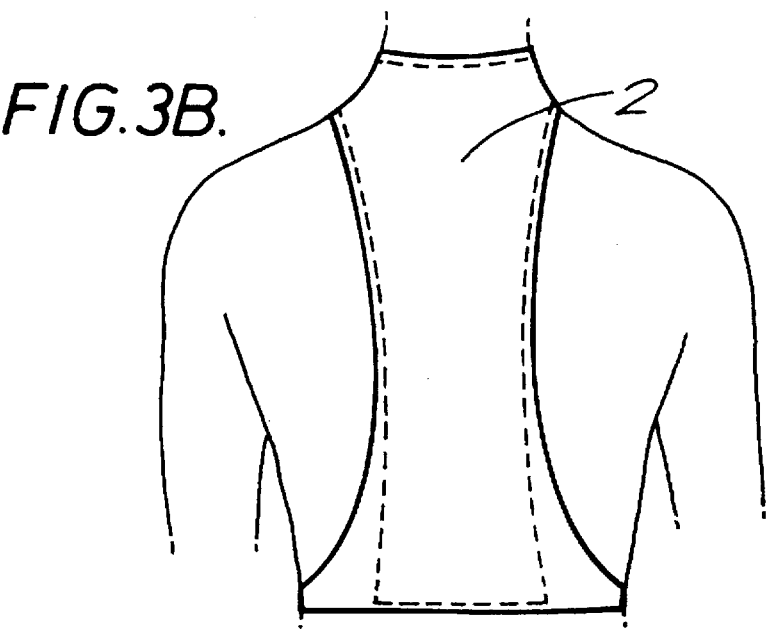

FIG. 3A shows a device for use in the upper thoracic or neck regions of a wearer, whilst FIG. 3B shows a device for use in the upper thoracic and/or mid-thoracic regions. In both cases, the dotted lines indicate the location of the insulating material 2. It will be seen that the insulating material is incorporated in modified undervests.

Figure 5:
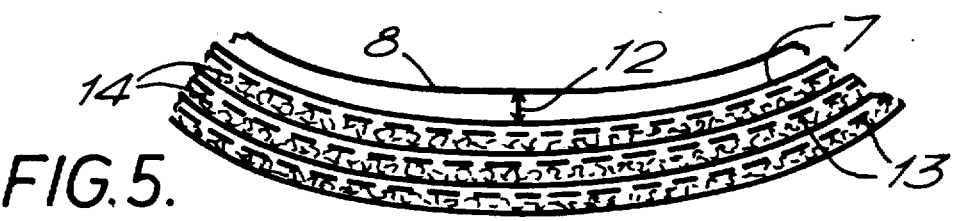
FIGS. 5 to 7 show cross-sectional views of various constructions of insulating material for embodiments of the invention.
Figure 6:
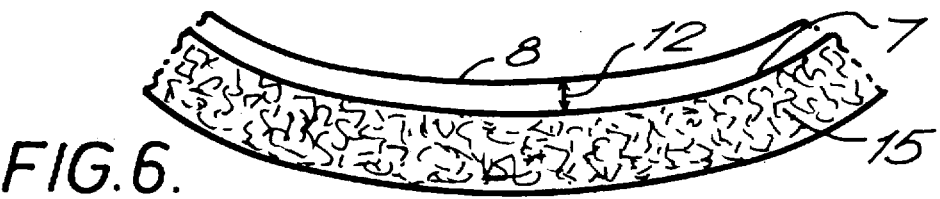
Figure 7:
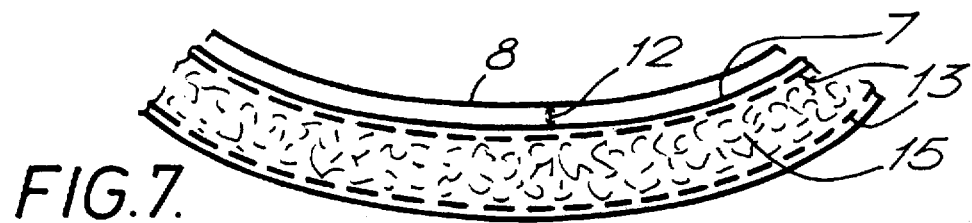

FIGS. 5 to 7 show various constructions for the insulating material.

FIG. 5 shows the posterior cross-section of the device with one particular design and arrangement of the insulating material in relation to the body. The insulating material is characterised by its organized lay-out. Several layers are shown. Each of them contains a perforated reflective layer 13 which has a reflective surface facing the skin backed by a convective insulation layer 14. The infrared reflective material used to reflect back infrared radiation emitted from the body is a metallised plastic or fabric film. The metal layer is conveniently a layer of aluminium of 200–750 Angstroms deposited through vacuum deposition and the substrate is conveniently made from polyester, polyvinylchloride, polypropylene or polyethylene of sub-millimeter thickness. This substrate material should not absorb water nor make substantial noise upon touching or movement.

Each layer 13 may alternatively be reflective on both sides thereof to further minimise heat loss. For example, a double-sided metallised layer may have a plastics substrate of 15 microns thickness disposed between two metal layers each 150–500 Angstrom thick. A plastics substrate between two metal layers serves as a micro-insulating medium similar to an electric capacitor.

To reduce convection and conduction heat losses this material is perforated with pores of 0.1–3 mm diameter, to a surface porosity of 2–40%. It can also be non-perforated but in an organised lay-out to allow fluid/air passage, for example as in an organised array of strips. This reflective layer is then backed with a convective heat loss reduction layer. Typically this is a microfibre or hollow fibre matrix known to have very high insulating values combined with lightweight and relatively low bulkiness. Typical microfibre or hollow fibre matrices are known under the trade names of Thinsulate® (3M Company, Minnesota, USA) or Hollofil® (ICI, UK). To minimise the overall heat losses the reflective layers backed by the insulating layers are organised themselves in multi-layers such that as viewed from the skin, the insulating materials have the following repeating sequence of layers: reflective layer/convective insulation layer/ reflective layer/convective insulation layer etc. The overall multilayer construction is contained in a thin porous fabric made conveniently of non-woven materials such as polypropylene.

The advantages of such an arrangement are that the proximity and conformity of the reflective and convective layers are ensured to maximise insulation efficiency and maintain the skin temperature high and constant. The distance 12 between the skin and the device is about or less than 10 mm to provide an effective insulation.

FIG. 6 shows an alternative design for the insulating material based on the use of a matrix made from a random array of metallised fibres 15. These fibres can be arranged in a random multilayer array. This matrix combines the properties of reflective, convective and conductive insulation. Commercially this is known under the trade name of Flectalon® and which is described in GB-A-1605045. The material functions as an equivalent to a reflective coating plus convection insulating layer. The multi-layer metallised fibre matrix of Flectalon® can be used with further reflective materials in the form of film with its reflective coating facing towards the body to ensure optimum radiation reflectance. Such a film may alternatively have a reflective coating on both sides thereof, as described above in relation to FIG. 5.

FIG. 7 shows an arrangement like FIG. 6 except that it has additional layers in an organised arrangement. The perforated reflective layers 13 are positioned with their reflective surfaces facing the skin and conforming to the skin to optimise insulation efficiency. Although the figure shows two layers 13 at the inner and outer enveloping layer it is understood that one layer might suffice. Alternatively more than two such layers may be provided. Again, the layers 13 may alternatively be reflective on both sides thereof.

Figure 8:
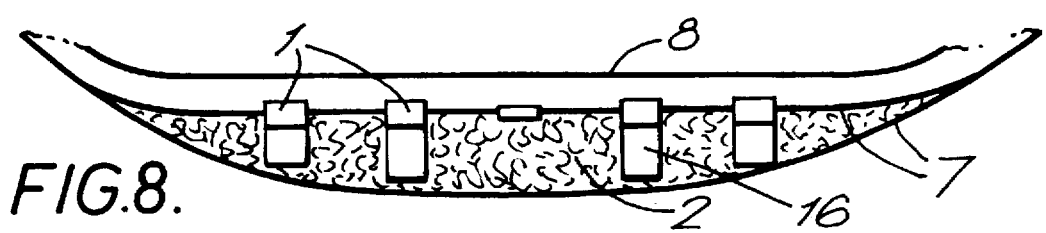
FIG. 8 shows a cross-section of a corset such as shown in FIGS. 1 to 3 which incorporates mechanical supports.

FIG. 8 is a cross-section of the device of FIGS. 1, 2 or 3 and shows the constructive arrangement for the mechanical support 1, the plastic foam spacers 16, the surrounding fabric 7 and the insulating material 2 in relation to the posterior body 8. To prevent the insulating material from being squashed and consequently reducing the convective insulation, plastic spacers 16 in the form of plastic foam strips are used as spacers and these are conveniently placed against the mechanical support strips. When for example the belt is tightened the thickness of the insulating material is maintained at least to the thickness of the spacers. Conveniently this is 5–10 mm. These plastic foam spacers are, for example, made from expanded polythene, making them lightweight and non-water retaining.

Figure 9:
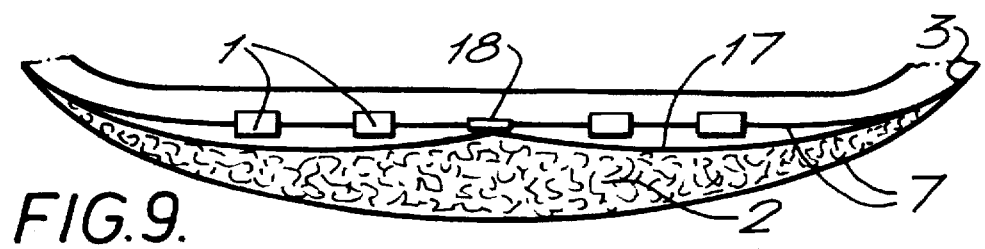
FIG. 9 shows a view similar to FIG. 8 of an alternative mechanical support arrangement.

FIG. 9 illustrates an alternative posterior cross-section arrangement of the device of FIG. 1 with an additional elasticated material 17 to enable a tighter fastening, in particular to enable the mechanical support strips 1 to conform more closely to the back of the body. Conveniently this elasticated material is attached to the longitudinal midline 18 of the device and can be stretched and fastened to the main part of the device. Tightening of the corset can be done by using the elasticated material 3 or the stretchable fabric 7 as shown respectively in FIGS. 1 and 2.

FIG. 10 shows the shape of a normal back with its curvatures, in particular along the spinal column area. The lumbar spinal column is seen from the outside as a long longitudinal groove 9 whereas the iliac wings 10 protrude at each side and join the column at the top of the sacrum. The curvature has an effect on the conformity and proximity between the insulating material and the body. A poor proximity and conformity (i.e. a large distance) reduces the efficiency of insulation and leads to a rapid decrease of the skin temperature upon cold exposure. As can be seen the corset is shaped so as to conform as closely as possible to the lumbar region.

There follows by way of non-limiting example the results of three trials carried out using embodiments of the present invention.

EXAMPLE 1

The skin temperature of the lumbar region of a healthy female volunteer near the spinal column covering the erector spinae muscles was measured at three different environmental temperatures. Three materials were used to cover the lumbar region after this has been exposed to the environmental temperature. The body was kept warm in all cases. In group 1 the materials were a cotton polo neck shirt and a thick wool jacket representing normal clothes, in group 2 the material was a conventional polyester insulating wadding of 15 mm loft (ie. thickness without compression) strapped against the body to provide close proximity and conformity (this group represents the control group based on convection and conduction insulation only) and in group 3 the material was the construction described in relation to FIG. 6 and which had only 10 mm loft. (Theoretically this should not be as good an insulator as the material of group 2 with 15 mm loft.) The results are as follows:

At 21.2° C. environmental temperature the skin temperatures of Group 1 and 2 were 34.5° C. and 34.5° C. respectively whereas it was 35.1° C. in group 3, an increase of 0.6° C. over the other groups. The skin temperature without any covering material was 32.9° C.

At 16.3° C. environmental temperature the skin temperatures of Group 1 and 2 were 33.3° C. and 33.6° C. respectively whereas it was 34.2° C. in group 3, an increase of 0.9° C. over the 'clothes' group and 0.6° C. over the wadding material. The skin temperature without any covering material was 30.8° C. Note that when it becomes colder groups 1 and 2 are below 34° C.

At 5.0° C. environmental temperature the skin temperatures of Group 1 and 2 were reduced to 31.8° C. and 32.4 C. respectively whereas it was still 34.2° C. in group 3, an increase of 2.4° C. over the 'clothes' group and 1.8° C. over the wadding material. The skin temperature without any covering material was 28.2° C. Note that when it becomes much colder, the temperatures in groups 1 and 2 are well below 33° C. whilst group 3 still displays the 34° C. level.

It should also be noted that those experiments represent worse conditions than normal living or working conditions. Under these conditions, Groups 2 or 3 materials are used with an additional overshirt or overcoat, improving their heating efficiency at colder environmental temperatures. Under those conditions the skin temperature of group 3 material reaches 35° C. at 5° C. environmental temperature as compared with less than 34° C. for group 2. A temperature level close to the core body temperature is believed to promote blood flow and keeps the muscles 'active', e.g. firing at a desired rate, amplitude and pattern. This is consistent with the finding that at transient low temperatures there is a vaso-constriction and the muscles feel 'stiff'.

EXAMPLE 2

In another experiment we tested the skin temperature of another volunteer under conditions similar to the above experiment 1. The device used for Example 2 is the same as that used for Example 1. It was tested against itself as follows: (1) in close proximity and conformity to the body; and (2) under loosely fitting conditions with respect to the body. This latter condition represented the use of the device as a piece of clothing. The distance between the lumbar skin and the fabric lining of the device was 10+/−3 mm in the second case as compared to 2 or 3 mm in the first case.

At an environmental temperature of 7.1° C. the skin temperature with the body-tight and body-conformed device embodying the present invention was 33.1° C. whereas that with the loose-fit was only 31.6° C. (the body conditions of the volunteer at the time of these experiments were somewhat different from those of Example 1 and hence the skin temperature with the device embodying the invention was only 33.1° C.). By putting additional clothes which one would wear to stay warm at that environment temperature, the skin temperatures were increased to 33.5° C. with the device embodying the invention but only 32.3° C. with the loosely fitting device.

EXAMPLE 3

Example 3 illustrates the benefits obtained with a device embodying the present invention. Human volunteers were exposed in a double-blind, confidential trial to two types of belt-like devices worn against the lumbar region of the spine, one type containing a material of low thermal conductivity (0.28 cm/TOG), a density of about 11 kg/cubic meter and another which was identical except that it had no insulating material (control placebo). The volunteers wore the device in winter (−4 to +10 degrees centigrade outdoor temperature). The results were, in statistical terms, that the volunteers wearing the device embodying the present invention with the insulating material of the mentioned conductivity value experienced less back pain, shorter duration of back pain and reduced absence from work due to back pain. For example based on a number of approximately 40 patients in each group the number of patients on sick leave for more than 30 days due to back trouble decreased from 3% to 0% when wearing the device with the insulating material. Also the percentage of patients with no back trouble increased from 33% before wearing the device embodying the present invention to 41% after wearing the device.

We claim:

1. A device for preventing or reducing the incidence or intensity of pain occurring in a region of the body of a wearer, said device being non-rigid and comprising insulating material with means designed for the material to conform with the contour of the body region and to be worn in close proximity with the body region, said insulating material having means for reducing heat loss from the body region by convection and reflective means for reducing heat loss from the body by radiation, said reflective means having a moisture permeable micro-porous structure providing multiple passage ways, so that said reflective means can allow the passage of water vapor therethrough while reflecting heat back to the body region, whereby a targeted reduction in heat loss from said body region is achieved such that the skin and underlying musculoskeletal structures are kept in an active state such that they can function properly to provide a clinical benefit to the body region.

2. A device as claimed in claim 1, wherein the insulating material has a thermal conductivity of less than 0.35 cm/TOG or 0.035 Watt/m° C.

3. A device as claimed in claim 1, wherein the insulating material has a density of less than 12 kg/cubic meter.

4. A device as claimed in claim 1, wherein the device is less than 2.0 cm thick.

5. A device as claimed in claim 1, wherein the microporous structure comprises a micro-perforated film.

6. A device as claimed in claim 5, wherein a plurality of perforated reflective layers and at least one insulation layer are provided, with a said relective layer being arranged at closest proximity to the wearer.

7. A device as claimed in claim 1, wherein elasticated or stretchable materials are used to ensure that the insulating material is in conformity and close proximity to the body.

8. A device as claimed in claim 1, wherein a mechanical support is provided in the form of strips or bands aligned parallel to the main axis of the body region.

9. A device as claimed in claim 1, wherein a mechanical support is provided in the form of strips or bands which criss-cross the main axis of the body region.

10. A device as claimed in claim 1, wherein said device forms part of an article, the article being selected from the group consisting of:

a belt for treating the back;

a collar for treating the posterior neck;

modified underwear incorporating the insulating material against the relevant body part such as the upper and mid-thoracic back;

a modified sports garment incorporating the insulating material against the relevant body part such as the upper and mid-thoracic back; and a device to be worn around a joint such as the knee, elbow or ankle.

11. A device as claimed in claim 1, wherein, in use, the skin temperature of the body region is maintained by the device at at least 33° C.

12. A device as claimed in claim 1, wherein said reflective means comprises at least one reflective layer constituted by an array of strips.

13. A device as claimed in claim 5, wherein said reflective film is constituted by aluminized plastic.

14. A device as claimed in claim 5, wherein said reflective layer is constituted by a fabric film.

15. A device as claimed in claim 1, wherein the region of the body of the wearer is the back region and the device has a central portion shaped so as to conform to the longitudinal spinal groove of a wearer.

16. A method of preventing or reducing the incidence or intensity of pain in a body region comprising:

providing a non-rigid device including insulating means having means for reducing heat loss from the body region by convection and reflective means for reducing heat loss from the body region by radiation, said reflective means having a moisture permeable microporous structure providing multiple passage ways so that said reflective means can allow the passage of water vapor through said reflective means while reflecting body heat toward the body region;

placing the device over the body region; and attaching the device to the body region such that the insulating means reduces heat loss from the body region and maintaining said reflective means no more than 10 mm (0.4 in) from said body region, whereby heat loss from the body portion is reduced to maintain the body portion temperature elevated while releasing moisture from the region between the body portion and the reflective means.

17. A device for preventing or reducing the incidence or intensity of pain occurring in a region of the body of a wearer, said device being non-rigid and comprising insulating material which is arranged to be worn in conformity and close proximity with the body region, said insulating material having means for reducing heat loss from the body region by convection and reflective means for reducing heat loss from the body by radiation, said reflective means being permeable so as to allow the passage of water vapor therethrough, whereby a targeted reduction in heat loss from said body region is achieved such that the skin and underlying musculoskeletal structures are kept in an active state such that they can function properly to provide a clinical benefit to the body region; and wherein the insulating material is a random multi-layered metallized plastic fiber matrix.

18. A device for preventing or reducing the incidence or intensity of pain occurring in a region of the body of a wearer, said device being non-rigid and comprising insulating material which is arranged to be worn in conformity and close proximity with the body region, said insulating material having means for reducing heat loss from the body region by convection and reflective means for reducing heat loss from the body by radiation, said reflective means being permeable so as to allow the passage of water vapor therethrough, whereby a targeted reduction in heat loss from said body region is achieved such that the skin and underlying musculoskeletal structures are kept in an active state such that they can function properly to provide a clinical benefit to the body region; and wherein spacers are provided to maintain the insulating material at a minimum thickness upon stretching or compression to thereby maintain insulation efficiency.

* * * * *